United States Patent [19]
Collins

[11] 4,338,841
[45] Jul. 13, 1982

[54] ENTRANCE TUBE FOR A SAMPLER FOR MOLTEN MATERIAL

[76] Inventor: William J. Collins, 7005 Madison St., Merrillville, Ind. 46410

[21] Appl. No.: 173,486

[22] Filed: Jul. 30, 1980

[51] Int. Cl.³ .............................................. G01N 1/20
[52] U.S. Cl. ................................. 73/863.52; 73/864.55
[58] Field of Search ........... 73/863.41, 863.51, 863.52, 73/863.53, 863.54, 863.55

[56] References Cited

U.S. PATENT DOCUMENTS

| | | | |
|---|---|---|---|
| 1,967,428 | 7/1934 | Quereau | 73/863.51 |
| 3,098,390 | 7/1963 | Bourne et al. | 73/863.51 |
| 4,002,071 | 1/1977 | Collins | 73/863.51 |

FOREIGN PATENT DOCUMENTS 697239  11/1964  Canada ............................. 73/863.41

*Primary Examiner*—S. Clement Swisher

[57] ABSTRACT

The invention involves a tube for use with a device for obtaining a sample of molten material and providing the tube with a notched entrance or receiving structure whereby to facilitate or promote the inflow of such a material through the tube and into such a device. In this regard, reference is hereby made to my copending application Ser. No. 075, 941 filed Sept. 17, 1979, now U.S. Pat. No. 4,297,902.

9 Claims, 8 Drawing Figures

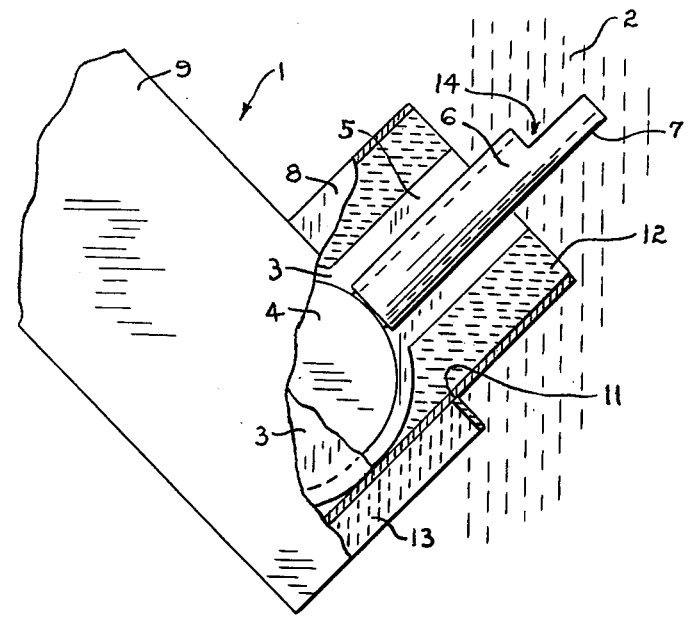
Fig.-1
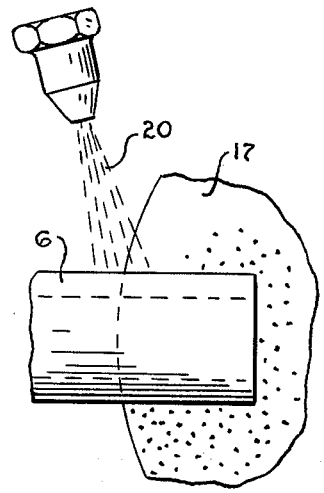
Fig.-3
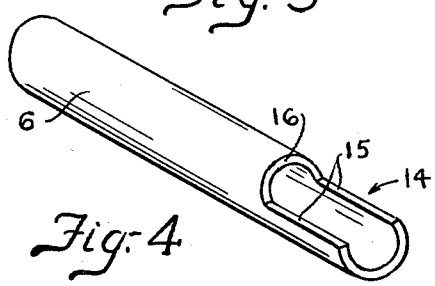
Fig.-4
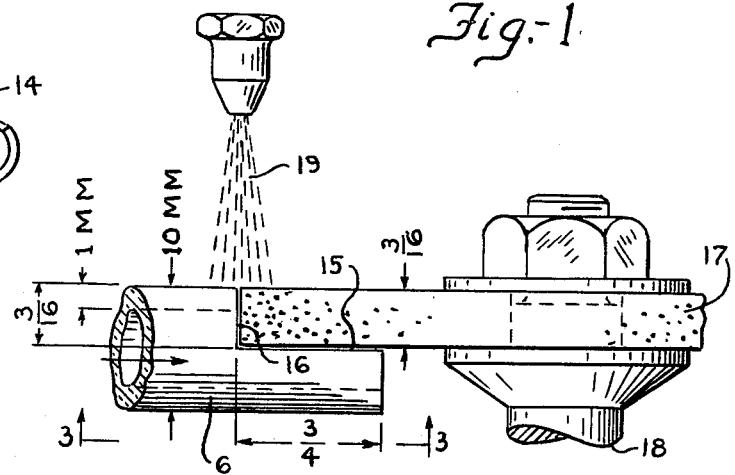
Fig.-2
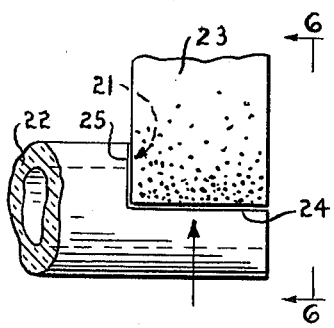
Fig.-5
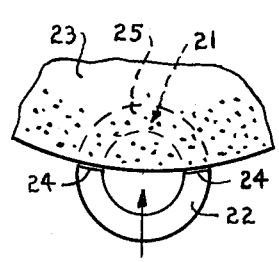
Fig.-6
Fig.-7
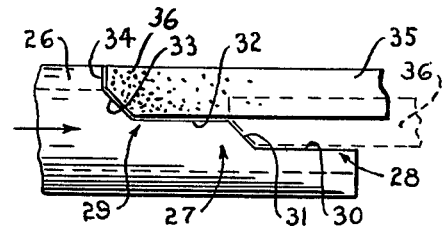
Fig.-8

ENTRANCE TUBE FOR A SAMPLER FOR MOLTEN MATERIAL

BACKGROUND OF THE INVENTION

An appreciable number of Patents have been issued with respect to devices for obtaining samples or quantities of molten material for testing purposes, such as molten metal, as evidenced by the following which include non-metallic tubular means for entry into a mass of such material to collect a sample or quantity of material therefrom for flow into receiving means or mold cavities of such devices: William J. Collins U.S. Pat. No. 3,415,124 dated Dec. 10, 1968; Kazuro Suzuki et al U.S. Pat. No. 3,513,903 dated May 26, 1970; William J. Collins U.s. Pat. No. 4,002,071 dated Jan. 11, 1977; Joseph J. Boron U.S. Pat. No. 3,751,986 dated Aug. 14, 1973 and Richard A. Falk U.S. Pat. No. 3,859,857 dated Jan. 14, 1975.

There are also additional Patents directed to tubes for different uses which are provided with bevelled entrances, including the following: Albert B. Welty U.S. Pat. No. 2,467,791 dated Apr. 19, 1949; Armin E. Reinert U.S. Pat. No. 2,475,857 dated July 12, 1949; Robert A. Stewart U.S. Pat. No. 3,175,554 dated Mar. 30, 1965; Robert W. Stacks U.S. Pat. No. 3,595,087 dated July 27, 1971; Michel J. Auphan et al U.S. Pat. No. 3,713,777 dated Jan. 30, 1973 and Narbick A. Karamian U.S. Pat. No. 3,713,778 dated Jan. 30, 1973.

OBJECTIVES OF THE INVENTION

In view of the above, the primary objective of the subject invention is to provide tubular means or tube embodying an improvement which is different from all of those illustrated in the above Patents. This improvement preferably comprises providing a fore extremity or entrance end of a tube with a notch, as distinguished from a funnel, an angled fore end, or a bevel.

More particularly, the object is to provide a tube which is preferably of a tubular cylindrical character and provided with a notch intersecting its entrance and whereby the entrance in the end and the notch, in combination provide a relatively large opening whereby to facilitate entry of molten material into the tube when the latter of a sampler device is inserted in a supply of such a material for obtaining a sample thereof.

A specific objective of the subject invention is to provide a tube or tubular means which, when utilized with a molten metal sampler, is preferably of a non-metallic character, such as glass, Pyrex or quartz.

Another object of the invention is to provide a tube which normally has a cylindrical tubular entrance and it is the material forming this entrance which is preferably interrupted by an elongated notch whereby to provide what may be termed a scoop, an elongated channel, a trough-like receiving means, an opening or an enlarged entrance, as distinguished from a straight bevelled entrance, as depicted, for example, in the Falk U.S. Pat. No. 3,859,857 identified above.

Another specific object is to provide entrance structures which constitute improvements over the structures illustrated in my copending application above referred to.

A further specific object is to provide a tube in which the notch is preferably defined by a pair of parallel longitudinally extending marginal edges and an inner transverse arcuate edge, the arrangement preferably being such that the longitudinal edges lie in a chordal plane so that the maximum cross-dimension of the channel is greater than the cross-dimension of the notch. Otherwise expressed, the longitudinal edges lie in a plane above the longitudinal axis of the tube, the purpose of which will be described more in detail subsequently.

A particularly important object is to provide entrance tubes which can be provided with modified forms of notches and produced by one or more different methods.

Additional objectives or attributes of the invention will become apparent after the description hereinafter set forth is considered in conjunction with the drawings annexed hereto.

DRAWINGS

FIG. 1 is a pictorial view, with portions of a sampler device in sections, to illustrate a mode for obtaining a sample of molten material from a supply thereof;

FIG. 2 is a top view showing one method of constructing a notch in an entrance tube;

FIG. 3 is a side view of the structure shown in FIG. 2 as indicated by the lines 3—3;

FIG. 4 is a perspective view of a tube which has been constructed in accordance with FIG. 2;

FIG. 5 is a partial view showing a different mode of constructing a notch in an entrance tube;

FIG. 6 is an end view of the structure shown in FIG. 5 in accord with line 6—6;

FIG. 7 illustrates a tube provided with a different or modified form of a notched entrance structure; and FIG. 8 depicts a method of constructing the entrance structure of FIG. 7.

DESCRIPTION

Referring to FIG. 1 there is disclosed a device generally designated 1 for obtaining a sample of molten metal from a supply 2. This device may be designed and constructed in various ways and includes a pair of mating recessed sections 3 in which form a chamber or cavity constituting a receiving means 4 and a tubular formation formed by a pair of channel portions 5 (one shown), an entrance tube 6 which has an inner extremity secured in the formation and an outer fore extremity or entrance end 7. The sections are fixedly mounted in a housing 8, the latter of which is mounted in a front extremity of a tubular member 9 and extends through an opening 11 therein so that the device is preferably held in a substantially transverse or perpendicular position with respect to the longitudinal axis of the member whereby to facilitate entry of the tube into the supply 2, when, for example, the supply or source is in the form of a falling stream. A lance (not shown) is adapted for detachable connection with the tubular member 9. A tubular member (not shown) of cellulose material may be disposed about the tubular formation formed by the channels 5 whereby to assist in holding the sections 3 assembled and a mass of cement 12 in the housing 8 may also be utilized for this purpose and an additional mass 13 may be located in the member 9 whereby to assist in protecting the device and assist in fixedly holding it to the member.

The entrance tube 6, as shown, which embodies the invention is preferably elongated and cylindrical in shape and its fore extremity is provided with an elongated notch generally designated 14 which is preferably defined by a pair of parallel longitudinally extending corresponding marginal edges 15 and an inner transversely disposed arcuate edge 16 whereby to form or provide an elongated trough, scoop, channel or chordal opening in order to facilitate entry of a molten material or fluid for flow into and through tube into the chamber 4 of the device. The depth of the notch is preferably somewhat less than one half of the internal diameter of the tube so that the curved side wall portions of the notch are of a sufficient extent whereby to alleviate breakage or fracture of the tube at the junction between the longitudinal edges 15 and arcuate edge 16. The width of the slot is also less than the internal diameter of the tube. Obviously, the depth and width of the notch can be made larger than shown but this would render the fore extremity of the tube more susceptible to accidental fracture.

The cross-sectional dimensions of the tube and the structure or character of the notch may be modified to suit different conditions of use. The tube when utilized as a component of a device as depicted for obtaining a sample of molten material from a stream thereof is preferably constructed to have an outside diameter of 10 mm and an inside diameter of 8 mm. The length of the notch shown in FIG. 2 is three fourths (¾") of an inch and its depth three sixteenths (3/16") inches.

The tubes may have outside diameters within a range of 5 to 10 mm and the lengths of the notches may be within a range of three eights (⅜") of an inch and three fourths (¾") inches. The aforestated dimensions are typical for use but may be modified, depending on the ultimate use of the device for obtaining a sample of molten material or other material where applicable.

The notch 14 may be designed and constructed by different methods of ways. As exemplified in FIG. 2, for example, the tube 6 is adapted to be grasped by an operator and moved generally in a radial direction so that that the fore end of the tube will engage the peripheral or annular surface of an abrasive wheel 17, the latter of which is rotatable about an axis of a shaft 18 which carries the wheel. The thickness of the wheel, preferably three sixteenths (3/16") of an inch, is such that it substantially determines the depth of the notch when the tube is directed against the wheel as shown. Obviously, the thickness and the diameter of a wheel may be varied as desired. A side spray or jet of water 19 is preferably utilized during the grinding or cutting of the tube whereby to facilitate the construction of the notch. If desired, a spray or jet 20 from an overhead location can be utilized as depicted in FIG. 3 in lieu of the side application of water in FIG. 2.

It is to be understood that if so desired, a fixture or jig, not shown, may be provided for holding a tube in position, in which event provision can be made for directing an abrasive wheel against the tube to construct the notch. In other words, the invention contemplates a setup or organization whereby the notch is constructed by correct relative movement between a tube and an abrasive wheel.

A modified mode or method of constructing a notch generally designed 21 in a tube 22 is illustrated in FIGS. 5 and 6. This modified method involves manipulating the tube broadside or sideways against the periphery of an abrasive wheel 23 as indicated by the directional arrows in these FIGURES. The wheel in this instance is preferably somewhat thicker. The notch 21 is defined by a pair of generally parallel longitudinally extending marginal side edges 24 and an inner marginal arcuate end edge 25. Due to the annular shape of the periphery of the wheel the longitudinal edges 24 will be slightly concave as shown in FIG. 6.

Another modified form of a notched tube 26 and method of constructing it are depicted in FIGS. 7 and 8. This tube is provided with a notch generally designated 27 which may be considered to be composed of a plurality of different smaller inner and outer notches generally designated 29 and 28 which are arranged in what may be termed a stepped, staggered or contiguous offset relationship. More specifically, in this regard, the outer notch 28 is defined by a pair of spaced longitudinal parallel marginal side edges 30 and a pair of rearwardly inclined marginal edges 31 and the inner and/or upper notch 29 is defined by a pair of spaced longitudinal edges 32, a pair of rearwardly inclined marginal edges 33 and an upright or transverse arcuate edge 34. It should be observed, by referring to FIG. 8 that the longitudinal edges 30 of the outer notch are disposed below the longitudinal axis of the tube and that the longitudinal edges 32 of the upper notch are disposed above this longitudinal axis or it may be stated that the aforesaid pairs of the longitudinal edges of the notches 28 and 29 are parallel to the axis and stradle the same. The notch 27 or the smaller notches 28 and 29 forming the notch 27 serve to provide a larger entrance, opening or receptive area for the molten material than that afforded by the notches 14 and 21 described above.

An abrasive wheel 35 is utilized to construct the notches 28 and 29 and as shown its periphery is designed and constructed or contoured to provide an annular portion which serves to successively form the notches 28 and 29 which in combination define the larger notch 27. More particularly, the tube 26 is manipulated twice to successively engage the annular portion 36 of the wheel to form the outer notch 28 and then the notch 29. If so desired, a wheel may be shaped so that the notches 28 and 29 can be substantially simultaneously constructed by manipulating the tube in only one continuous direction against the wheel, as distinguished from the two operations required when the wheel 35 is utilized. In other words, the wheel 35 is constructed to include a pair of portions 36 which are integral therewith. Obviously, the use of a spray or jet of water would be employed in the construction of the notches of FIGS. 7 and 8. It is to be understood that the notch 27 can also be constructed by moving the wheel to engage the tube 26 when the latter is held, for example, in a suitable fixture.

In view of the foregoing it is manifest that the invention or inventions shown and described offer tubes which are considered to constitute meritorious improvements over all of the above listed Patents.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. An elongated tube for the purpose described having a marginal end edge portion defining an entrance at one end of the tube for receiving a fluid, and a pair of offset contiguous notches of different depths provided in said tube adjacent said entrance whereby to facilitate entry of the fluid into the tube.

2. The tube defined in claim 1, in which at least one of the notches intersects said edge portion and the notches are arranged to provide side openings in the tube for simultaneously receiving the fluid.

3. The tube defined in claim 1, in which each of said notches is defined in part by a pair of longitudinal marginal edges.

4. The tube defined in claim 1, in which at least one of said notches is defined by a pair of longitudinal marginal edges and a transverse edge.

5. A device for obtaining a sample of molten material from a supply thereof, said device comprising an elongated outer housing having a front extremity, wall structure provided at said extremity forming a chamber for receiving such a material, a non-metallic tube communicatively connected to said chamber and having an outer extremity having an end entrance for initially receiving such a material for flow into said chamber, said tube having a notch intersecting said entrance serving to enlarge the entrance whereby to facilitate entry of such material into the tube, and said housing having a rear extremity for attachment to a lance.

6. A method which consists in providing wall structure forming a tube for receiving a fluid for flow therethrough, and then grinding a notch lengthwise in the wall structure at one end of the tube to provide an enlarged entrance opening whereby to facilitate entry of a fluid into the tube.

7. The device defined in claim 5, in which the tube is cylindrical and the depth of the notch is less than the diameter of the tube.

8. The device defined in claim 5, in which the tube is cylindrical and has an outside diameter within a range of 5 mm to 10 mm, inclusive, and the depth of the notch is less then the diameter of the tube.

9. The device defined in 5, in which the depth of the notch is less than the diameter of the tube and its length is within a range of three eighths to three fourths of an inch, inclusive.

* * * * *